(12) United States Patent
Burk

(10) Patent No.: US 8,389,566 B2
(45) Date of Patent: Mar. 5, 2013

(54) PROSTAGLANDINS AND ANALOGUES AS AGENTS FOR LOWERING INTRAOCULAR PRESSURE

(75) Inventor: Robert M. Burk, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/971,221

(22) Filed: Dec. 17, 2010

(65) Prior Publication Data

US 2011/0152797 A1 Jun. 23, 2011

Related U.S. Application Data

(62) Division of application No. 11/556,055, filed on Nov. 2, 2006, now Pat. No. 7,863,318.

(60) Provisional application No. 60/733,117, filed on Nov. 3, 2005.

(51) Int. Cl.
*A61K 31/38* (2006.01)
*A61K 31/34* (2006.01)

(52) U.S. Cl. ........ 514/438; 514/443; 514/454; 514/461; 514/472

(58) Field of Classification Search .................. 514/438, 514/461, 530, 570, 573; 549/61, 77–79
See application file for complete search history.

(56) References Cited

U.S. PATENT DOCUMENTS

| 5,352,708 A | 10/1994 | Woodward et al. |
| 5,741,810 A | 4/1998 | Burk |
| 5,834,498 A | 11/1998 | Burk |
| 6,124,344 A * | 9/2000 | Burk .............................. 514/438 |
| 6,160,129 A * | 12/2000 | Burk .............................. 549/61 |
| 6,248,773 B1 * | 6/2001 | Burk .............................. 514/438 |
| 6,391,872 B1 * | 5/2002 | Marfat ........................ 514/218 |
| 6,476,064 B1 | 11/2002 | Old et al. |
| 6,734,206 B1 | 5/2004 | Old et al. |
| 6,747,037 B1 | 6/2004 | Old et al. |

FOREIGN PATENT DOCUMENTS

| DE | 2626888 | 4/1977 |
| DE | 2719244 | 11/1977 |
| EP | 0283151 A2 | 9/1988 |
| GB | 1601994 | 4/1978 |
| JP | 53135955 | 11/1978 |
| WO | WO/9002553 | 3/1990 |
| WO | WO/94/06432 | 3/1994 |
| WO | WO 9526729 | 10/1995 |
| WO | WO 99/25358 | 5/1999 |

* cited by examiner

*Primary Examiner* — Michael G Hartley
*Assistant Examiner* — Jagadishwar Samala
(74) *Attorney, Agent, or Firm* — Kevin J. Forrestal; John E. Wurst; Doina G. Ene

(57) ABSTRACT

The present invention relates to cyclopentane heptenoic acid-5-cis-2-(3α-hydroxy or lower alkyloxy-5-thienylpentyl)-3, 5-dihydroxy, [1α, 2β, 3α, 5α] compounds, lower alkyl, hydroxyl lower alkyl and indole lower alkyl amides and esters thereof as potent ocular hypotensives that are particularly suited for the management of glaucoma.

19 Claims, No Drawings

PROSTAGLANDINS AND ANALOGUES AS AGENTS FOR LOWERING INTRAOCULAR PRESSURE

CROSS REFERENCE TO RELATED APPLICATIONS

This application is a Divisional of U.S. patent application Ser. No. 11/556,055, filed Nov. 2, 2006, which claims the benefit of claims the benefit of, U.S. Provisional Application No. 60/733,117, filed Nov. 3, 2005, each of which is incorporated herein by reference.

BACKGROUND OF THE INVENTION

1. Field of the Invention

The present invention relates to cyclopentane heptenoic acid-5-cis-2-(3α-hydroxy or lower alkyloxy-5-thienylpentyl)-3,5-dihydroxy, [1α, 2β, 3α, 5α] compounds lower alkyl, hydroxyl lower alkyl and indole lower alkyl amides and esters thereof as potent ocular hypotensives that are particularly suited for the management of glaucoma.

2. Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

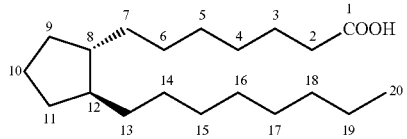

Various prostaglandin derivatives, e.g. latanoprost, travoprost, unoprostone isopropyl, etc. have been commercialized for lowering intraocular pressure and managing glaucoma. Recently, a prostamide, i.e. bimatoprost, has been marketed for treating increased eye pressure caused by open-angle glaucoma or ocular hypertension. Prostamides are structurally similar to prostaglandins but are biologically different. Prostamides, unlike prostaglandins, do not lower intraocular pressure by interaction with the prostaglandin receptor. (See U.S. Pat. No. 5,352,708, which hereby is incorporated by reference in its entirety.)

While prostaglandins and prostamides are effective in lowering intraocular pressure without significant intraocular side effects, ocular surface (conjunctival) hyperemia and foreign-body sensation have been associated with the topical ocular use of such compounds, in particular $PGF_{2\alpha}$ and its prodrugs, e.g., its 1-isopropyl ester, in humans.

Thus, it would be desirable to discover a prostamide or prostaglandin compound which effectively lowers intraocular pressure while not causing excessive hyperemia.

SUMMARY OF THE INVENTION

The present invention concerns a method of treating ocular hypertension which comprises administering to a mammal having ocular hypertension a therapeutically effective amount of a compound selected from the group consisting of compounds represented by the following formula:

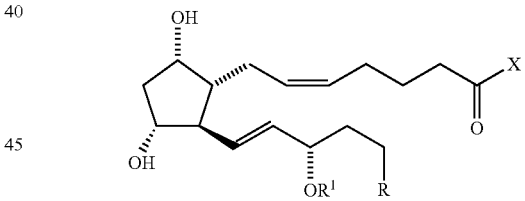

wherein $R^1$ is H or methyl;
R is selected from the group consisting of thienyl and substituted thienyl, wherein the substituent may be one or more radicals selected from the group consisting of fluoro, chloro, bromo, methyl and phenyl and X is selected from the group consisting of

wherein $R^2$ is H or methyl and $R^3$ comprises a substituted hydrocarbyl radical, including from 1 to 12 carbon atoms and at least one oxygen atom, e.g. as an ether or a hydroxyl moiety, and, optionally, a nitrogen atom. That is $R^3$ may be an alkylhydroxy radical or an alkyl ether or a hydroxy indole radical. Thus, $R^3$ may be an alkyl or an aryl radical which includes an oxygen atom as a hydroxy, alkyloxy, oxo, oxa moiety, etc. Preferably, $R^3$ is selected from the group consisting of 2-butyl-4-hydroxy, methoxy, 2-ethylhydroxy, and (2-ethyl)(5-hydroxy)indole.

Preferably, said thienyl is substituted with two chloro radicals, or two bromo radicals or one chloro and one methyl radical.

More preferably, when said thienyl is substituted with two chloro radicals, $R^2$ is H and $R^3$ is 2-ethylhydroxy, or when said thienyl is substituted with two bromo radicals, $R^2$ is methyl and $R^3$ is methoxy, or when said thienyl is substituted with one chloro radical and one methyl radical, $R^2$ is H and $R^3$ is (2-ethyl) (5-hydroxy) indole.

Most preferably said compound is selected from the group consisting of the following compounds.

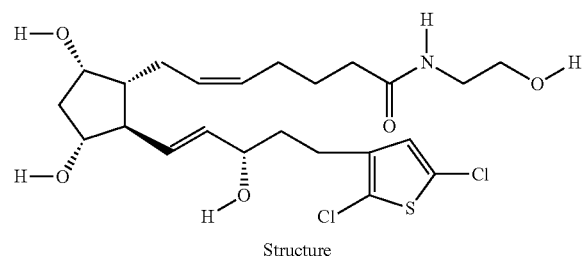

Structure

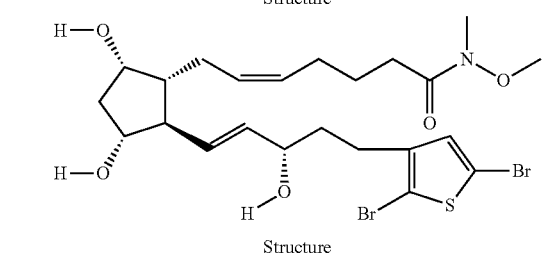

Structure

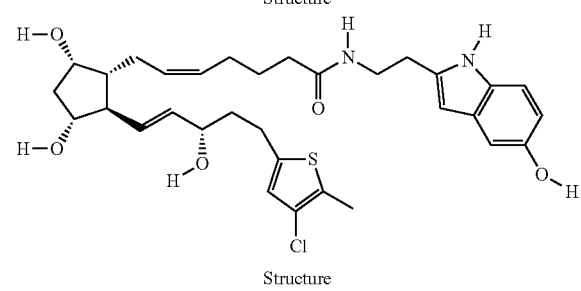

Structure

The compounds are very selective FP agonists.

Preferably R is substituted with two or more, e.g. 3, of said radicals.

These compounds effectively lower intraocular pressure while having lower hyperemia.

In another aspect of the invention, a ophthalmic solution comprising one or more of the above compounds in combination with an ophthalmically-acceptable vehicle is contemplated.

In a still further aspect, the present invention relates to a pharmaceutical product, comprising a container adapted to dispense its contents in a metered form; and an ophthalmic solution therein, as hereinabove defined.

Finally, certain of the above compounds disclosed herein and utilized in the method of the present invention are novel and unobvious.

DETAILED DESCRIPTION OF THE INVENTION

The above compounds of the present invention may be prepared by methods that are known in the art. For example, see U.S. Pat. Nos. 5,834,498; 5,741,810 and 6,124,344 to Burk, which are hereby incorporated by reference.

The compounds of the present invention were tested for in vitro activity as described in U.S. Pat. Nos. 6,734,206 and 6,747,037 to Old et al which are incorporated by reference.

For the most preferred compounds the in-vitro activity is as follows:

TABLE 1

| FUNCTIONAL_HFP 10.0000 | FUNCTIONAL_HTP 300.0000 | FEFP_EP4_RATIO 0.0030 |
|---|---|---|
| FUNCTIONAL_HEP1 98.0000 | FUNCTIONAL_HIP 50000.0000 | GPEP1 |
| FUNCTIONAL_HEP2 50000.0000 | FUNCTIONAL_HDP 50000.0000 | GPEP3 |
| FUNCTIONAL_HEP3A 50000.0000 | FEFP_OHL 0.2000 | RTTPVASC |
| FUNCTIONAL_HEP4 50000.0000 | RBEPVASC_EP4 80.0000 | HTPPLAT |
| FUNCTIONAL_HFP 37.0000 | FUNCTIONAL_HTP 374.0000 | FEFP_EP4_RATIO 0.0480 |
| FUNCTIONAL_HEP1 599.0000 | FUNCTIONAL_HIP 50000.0000 | GPEP1 |
| FUNCTIONAL_HEP2 50000.0000 | FUNCTIONAL_HDP 50000.0000 | GPEP3 |
| FUNCTIONAL_HEP3A 50000.0000 | FEFP_OHL 7.0000 | RTTPVASC |
| FUNCTIONAL_HEP4 50000.0000 | RBEPVASC_EP4 147.0000 | HTPPLAT |
| FUNCTIONAL_HFP 8.5000 | FUNCTIONAL_HTP 1140.0000 | FEFP_EP4_RATIO |
| FUNCTIONAL_HEP1 167.0000 | FUNCTIONAL_HIP 50000.0000 | GPEP1 |
| FUNCTIONAL_HEP2 50000.0000 | FUNCTIONAL_HDP 50000.0000 | GPEP3 |
| FUNCTIONAL_HEP3A 50000.0000 | FEFP_OHL 9.3000 | RTTPVASC |
| FUNCTIONAL_HEP4 50000.0000 | RBEPVASC_EP4 | HTPPLAT |

Ophthalmic solutions may be prepared by combining a therapeutically effective amount of at least one compound according to the present invention, or a pharmaceutically acceptable acid addition salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the ophthalmic solutions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
|---|---|
| active ingredient | about 0.001-5 |
| preservative | 0-0.10 |
| vehicle | 0-40 |
| tonicity adjuster | 1-10 |
| buffer | 0.01-10 |
| pH adjuster | q.s. pH 4.5-7.5 |
| antioxidant | as needed |
| surfactant | as needed |
| purified water | as needed to make 100% |

The actual dose of the active compounds of the present invention depends on the specific compound; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

Certain of the compounds of this invention are useful in treating other diseases and conditions which are responsive to prostaglandin analogues, e.g. cardiovascular; e.g. acute myocardial infarction, vascular thrombosis, hypertension, pulmonary hypertension, ischemic heart disease, congestive heart failure, and angina pectoris; pulmonary-respiratory; gastrointestinal; reproductive and allergic diseases; osteoporosis and shock.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof.

What is claimed is:

1. An ophthalmic solution comprising

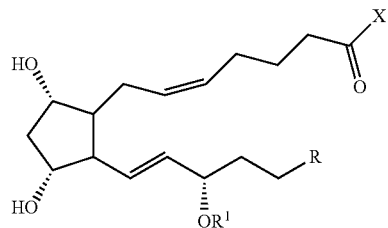

wherein $R^1$ is H or methyl;

R is selected from the group consisting of thienyl and substituted thienyl, wherein the substituent may be one or more radicals selected from the group consisting of fluoro, chloro, and phenyl and X is selected from the group consisting of

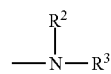

wherein $R^2$ is H or methyl and $R^3$ comprises a substituted hydrocarbyl radical, including from 1 to 12 carbon atoms and at least one oxygen atom, and, optionally, a nitrogen atom.

2. A pharmaceutical product comprising a container adapted to dispense its contents in a metered form and the ophthalmic solution of claim 1.

3. The pharmaceutical product of claim 2, comprising:

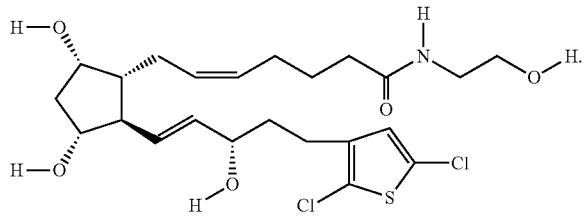

4. The pharmaceutical product of claim 2, comprising:

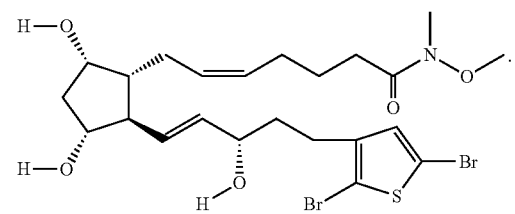 [SMILES: CON(C)C(=O)CCC/C=C\C[C@@H]1[C@@H](/C=C/[C@@H](O)CCc2cc(Br)sc2Br)[C@H](O)C[C@@H]1O]

5. The pharmaceutical product of claim 2, comprising:

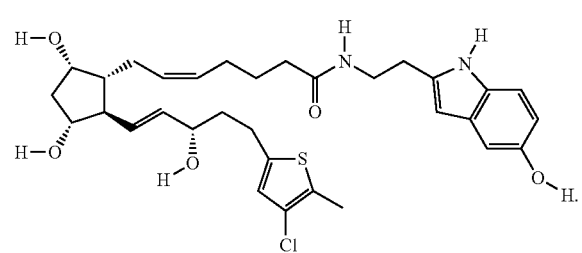

6. The ophthalmic solution of claim 1, wherein $R^2$ is H.

7. The ophthalmic solution of claim 1, wherein $R^3$ is 2-ethylhydroxy, methoxy, or (2-ethyl)(5-hydroxy)indole.

8. The ophthalmic solution of claim 1, wherein the thienyl is substituted with two chloro substituents, or one chloro and one methyl substituent.

9. The ophthalmic solution of claim 1, comprising:

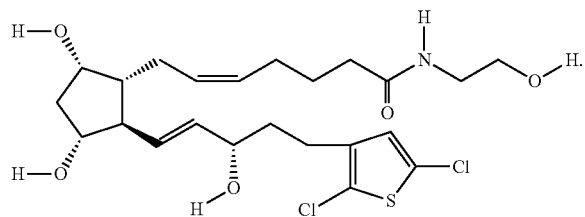

10. The ophthalmic solution of claim 1, comprising:

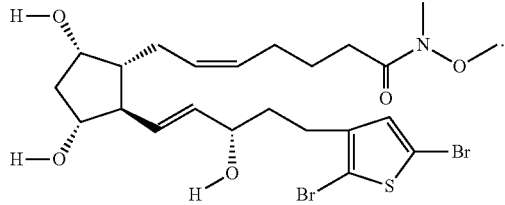 [SMILES: CON(C)C(=O)CCC/C=C\C[C@@H]1[C@@H](/C=C/[C@@H](O)CCc2cc(Br)sc2Br)[C@H](O)C[C@@H]1O]

11. The ophthalmic solution of claim 1, comprising:

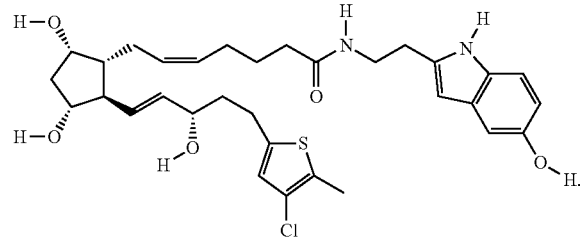

12. A novel compound selected from the group consisting of

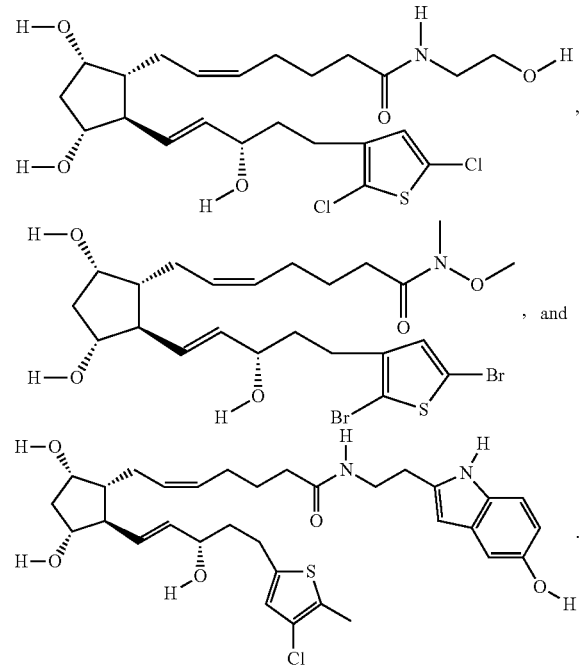

13. The novel compound of claim 12, represented by a formula:

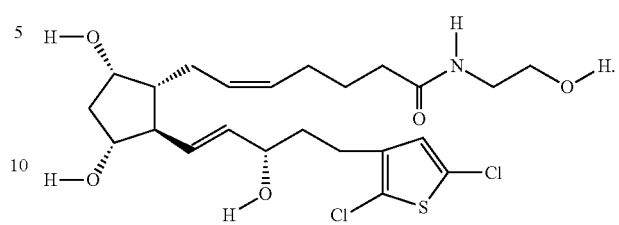

14. The novel compound of claim 12, represented by a formula:

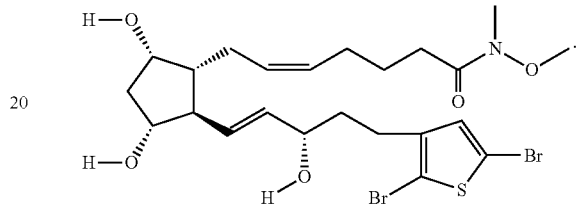

15. The novel compound of claim 12, represented by a formula:

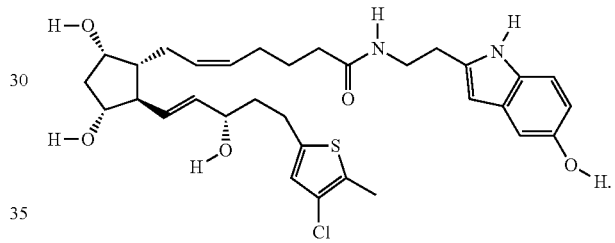

16. A compound comprising

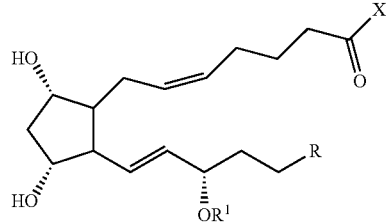

wherein $R^1$ is H or methyl;
R is thienyl optionally substituted with one or more substituents, wherein each substituent is independently fluoro, chloro, bromo, methyl or phenyl; and
X is

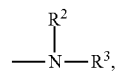

wherein $R^2$ is H or methyl and $R^3$ is a $C_{1-12}$ ether or comprises a hydroxy indole.

17. The compound of claim 16, wherein $R^2$ is H.
18. The compound of claim 16, wherein $R^2$ is methyl.
19. The compound of claim 16, wherein $R^3$ is methoxy, or (2-ethyl)(5-hydroxy)indole.

* * * * *